(12) United States Patent
Matsuoka et al.

(10) Patent No.: US 8,465,501 B2
(45) Date of Patent: Jun. 18, 2013

(54) LIGATING APPARATUS

(75) Inventors: Yoshiaki Matsuoka, Kanagawa (JP); Koji Itoh, Kanagawa (JP); Masayuki Iwasaka, Kanagawa (JP); Ryosuke Osako, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 200 days.

(21) Appl. No.: 13/017,410

(22) Filed: Jan. 31, 2011

(65) Prior Publication Data
US 2011/0245855 A1 Oct. 6, 2011

(30) Foreign Application Priority Data

Mar. 30, 2010 (JP) ................................. 2010-079913

(51) Int. Cl.
*A61B 17/08* (2006.01)
(52) U.S. Cl.
USPC .......................................... 606/142; 606/157
(58) Field of Classification Search
USPC .................. 227/901–902; 606/139, 142–143, 606/157–157, 157–158
See application file for complete search history.

(56) References Cited

U.S. PATENT DOCUMENTS 6,814,742 B2 * 11/2004 Kimura et al. ................ 606/151

FOREIGN PATENT DOCUMENTS

| DE | 197 07 382 A1 | 9/1997 |
|---|---|---|
| JP | 2007-136128 A | 6/2007 |
| JP | 2007-209775 A | 8/2007 |
| WO | 03/030746 A1 | 4/2003 |
| WO | 2009/136397 A2 | 11/2009 |

OTHER PUBLICATIONS

Extended European Search Report Jul. 21, 2011.

* cited by examiner

*Primary Examiner* — Darwin Erezo
*Assistant Examiner* — Shaun L David
(74) *Attorney, Agent, or Firm* — McGinn IP Law Group, PLLC

(57) ABSTRACT

A ligating apparatus includes a clip, a clip connecting member, a clip holding member, an operating wire, an inner sheath member, an outer sheath member and first and second movement restricting portions. The clip ligates a body tissue with arm portions. The clip connecting member connects to a clip base portion. The clip connecting member is inserted through the clip holding member. The operating wire connects to the clip connecting member. The inner sheath member encloses the operating wire to support the clip holding member. The outer sheath member covers an outer periphery of the inner sheath member and freely advances and retreats. The outer sheath member advances and/or retreats to change the degree of opening of the arm portions. The first movement restricting portion restricts the inward movement of the clip holding member. The second movement restricting portion restricts the outward movement of the clip holding member.

9 Claims, 11 Drawing Sheets

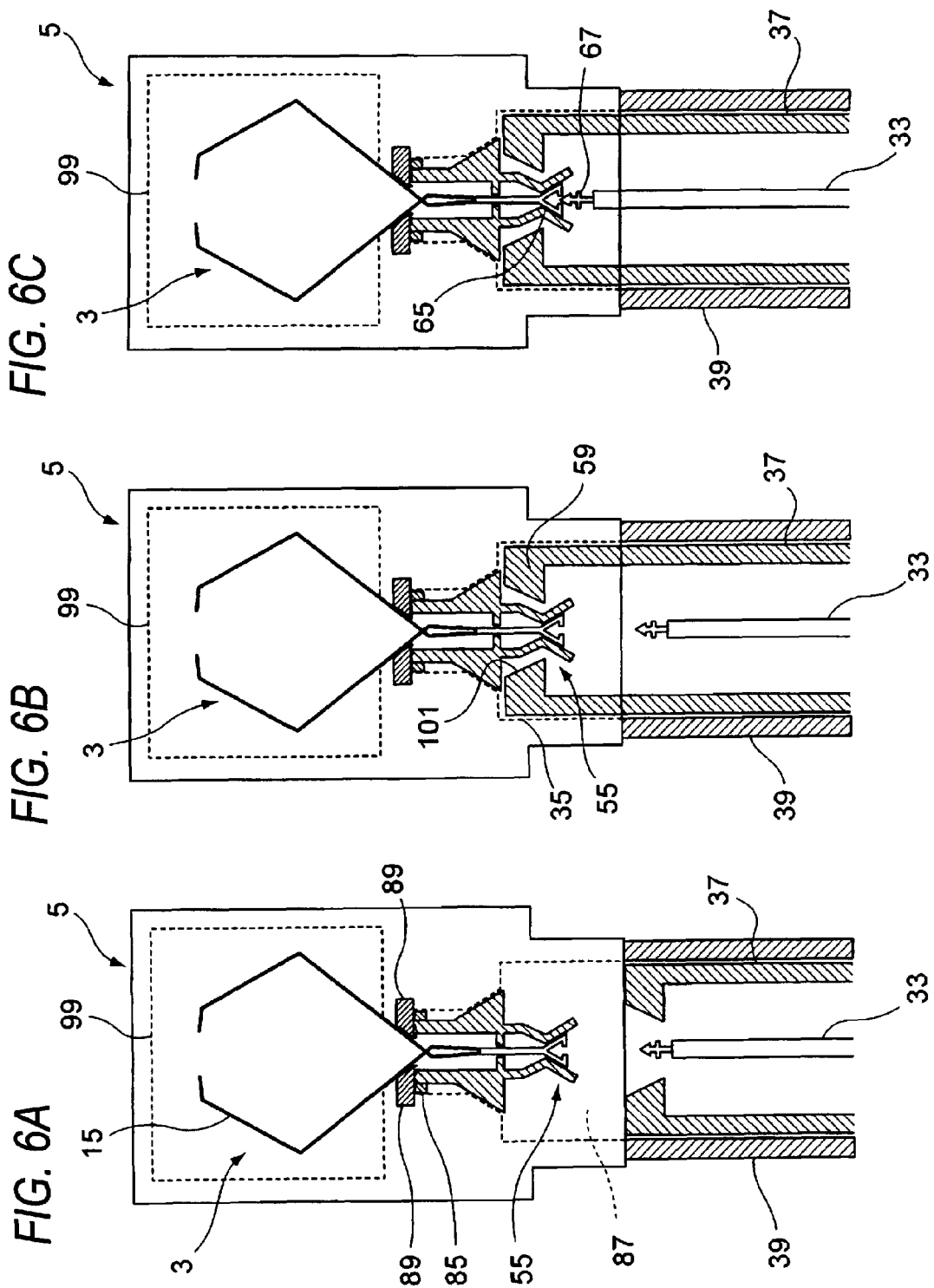

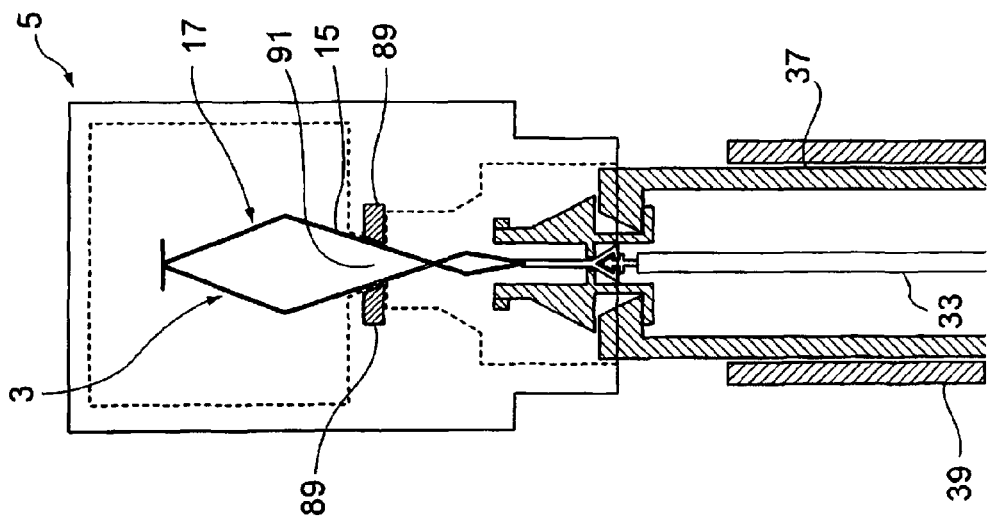
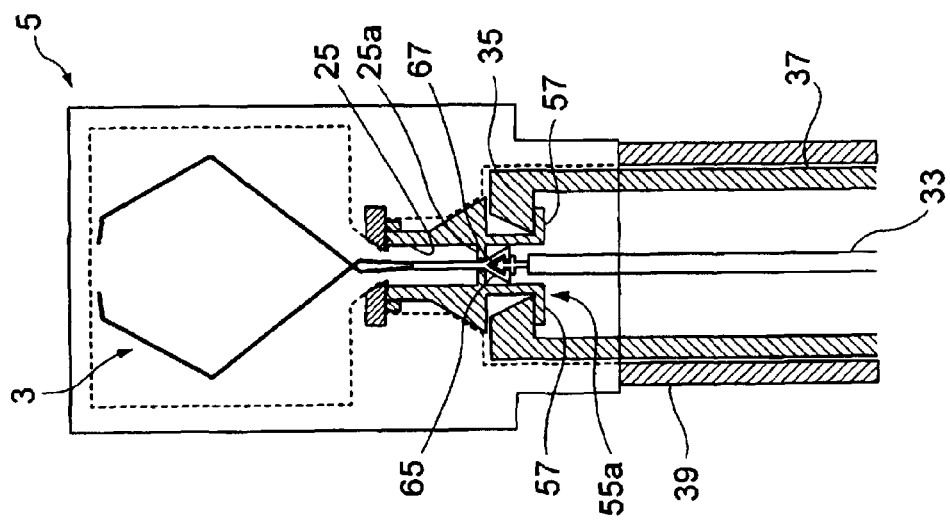
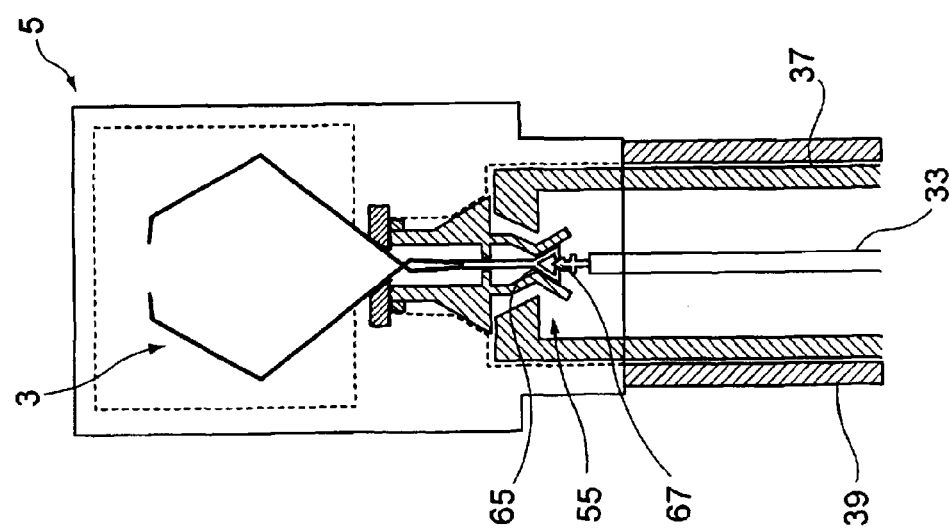

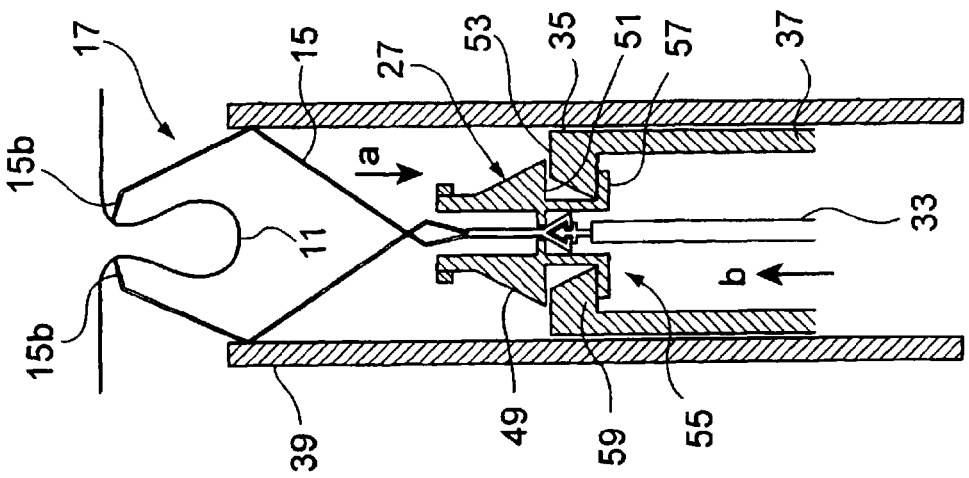
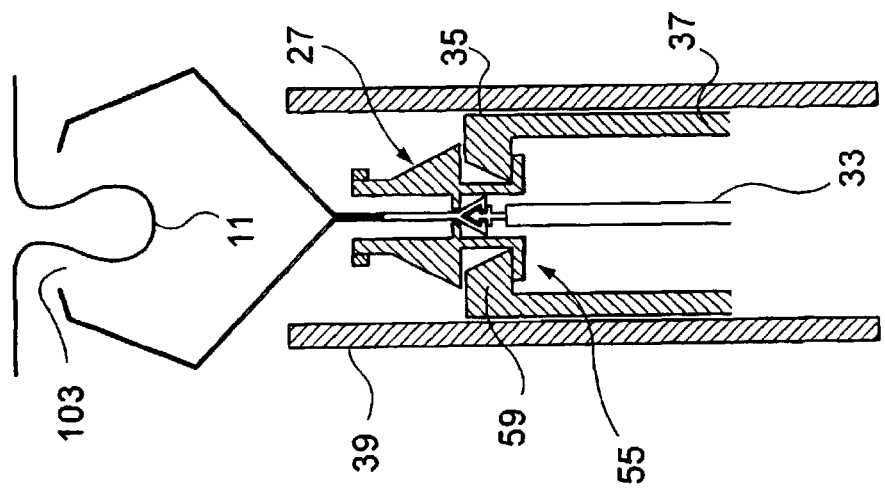
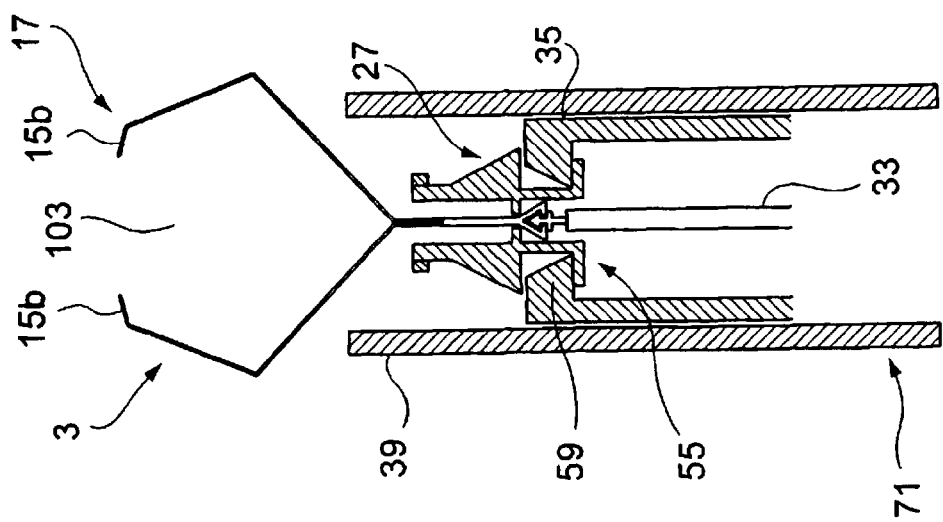

FIG. 10A
FIG. 10B
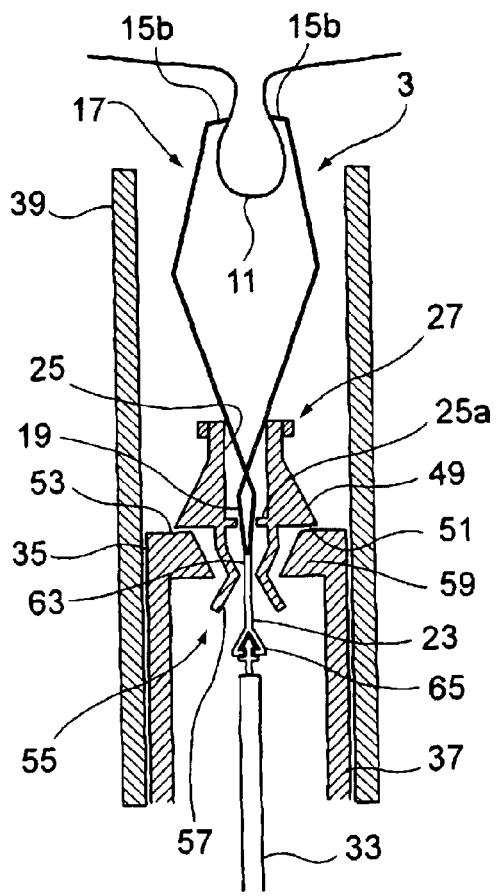
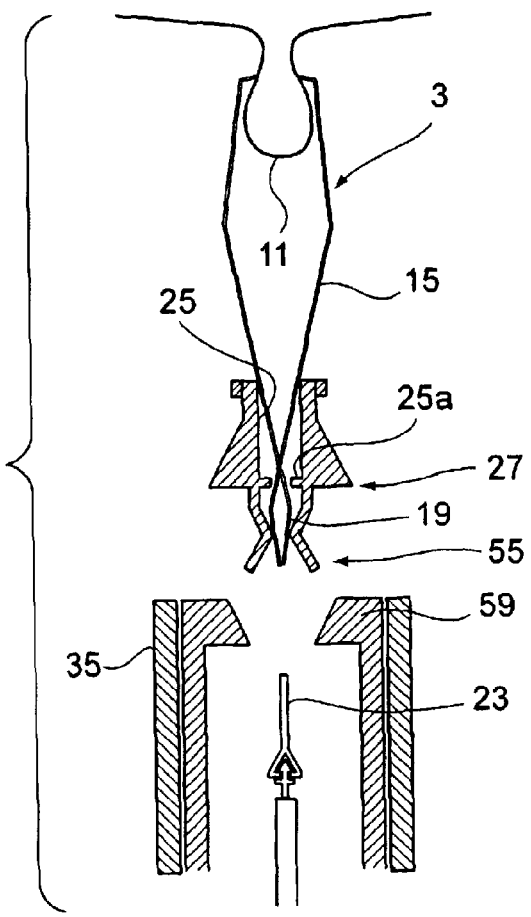

LIGATING APPARATUS

CROSS-REFERENCE TO RELATED APPLICATIONS

This application claims the benefit of Japanese Patent Application No. 2010-079913, filed on Mar. 30, 2010, the entire contents of which are hereby incorporated by reference, the same as if set forth at length.

BACKGROUND OF THE INVENTION

1. Technical Field

The present invention relates to a ligating apparatus for ligating a body tissue.

2. Description of Related Art

An apparatus to be inserted from, e.g., a forceps opening of an endoscope into a body cavity and ligate a desired body tissue by adjusting a clip to the position of the body tissue and then performing advancing/retreating operations of an operating wire to close the clip is known as a ligating apparatus for ligating a body tissue (see, e.g., JP-A-2007-209775 and JP-A-2007-136128). According to a configuration described in JP-A-2007-209775, the ligating apparatus is pulled out of the body cavity while the clip once ligating the tissue is separated from the operating wire and remains placed in the body cavity. Then, an unused clip is taken out of a clip case that accommodates unused clips, and attached to an end of the ligating apparatus. After that, the ligating apparatus is inserted into the body cavity again. Consequently, the ligating apparatus is configured such that a plurality of clips can successively be used to ligate body tissues.

However, the above ligating apparatus is such that after a clip is once closed, the clip cannot be opened again due to the structure of the clip. Thus, when a body tissue is clipped with the clip, it is necessary to carefully adjust the position of the clip so that the clip is positioned at a desired place and directed in a desired direction. Accordingly, a ligating operation of a clip requires skill.

A double sheath configuration described in JP-A-2007-136128, in which an inner sheath member and an outer sheath member are arranged outside an operating wire, is such that if the inner sheath member is not fixed to the operating wire, a clip slips off when the outer sheath member is caused to run out with respect to the inner sheath member. Thus, during an operation of causing the outer sheath member to run out, a surgical procedure is complicated. This becomes a factor that reduces usability.

SUMMARY

An object of the invention is to provide a ligating apparatus which can freely perform opening/closing of a clip when performing an operation of ligating a body tissue, and which can re-grasp the tissue by a simple operation.

The invention includes the following configuration.

A ligating apparatus for ligating a body tissue includes a clip, a clip connecting member, a clip holding member, an operating wire, an inner sheath member, an outer sheath member and first and second movement restricting portions. The clip has freely openable/closable arm portions and configures to ligate a body tissue with the arm portions. The clip connecting member has a connecting member end portion connected continuously to a clip base portion. The clip holding member has a communicating hole for causing the clip and the clip connecting member to be inserted into the communicating hole. The operating wire connects to a wire connecting portion provided at a connecting member base portion of the clip connecting member and is configured to perform an operation of pulling the clip connecting member. The inner sheath member is configured to be extended to enclose the operating wire and supports the clip holding member at a distal-end portion of the inner sheath member. The outer sheath member is arranged to cover outer periphery of the inner sheath member and is arranged to freely advance and retreat. The first and second movement restricting portions are configured to restrict movements of the clip holding member with respect to the inner sheath member. The outer sheath member changes a degree of opening of the arm portions by causing the arm portions to abut on an inner peripheral surface of the outer sheath member. The first movement restricting portion restricts movement of the clip holding member from an axially outer side to an axially inner side. The second movement restricting portion restricts movement of the clip holding member from an axially inner side to an axially outer side.

The ligating apparatus according to the invention can freely perform opening/closing of a clip when performing an operation of ligating a body tissue, and can re-grasp the tissue by a simple operation.

BRIEF DESCRIPTION OF THE DRAWINGS

FIG. 6A is a cross-sectional view illustrating a primary part of the ligating apparatus at the position-adjustment of an operating device and the clip unit. FIG. 6B is a cross-sectional view illustrating the primary part at the projecting of an inner sheath member. FIG. 6C is a cross-sectional view illustrating the primary part at the abutment of a wire.

FIG. 7A is a cross-sectional view illustrating a primary part of the ligating apparatus at the start of pressing the wire. FIG. 7B is a cross-sectional view illustrating the primary part at the opening of an elastically bending leg-element. FIG. 7C is a cross-sectional view illustrating the primary part at the taking-out of the clip unit from the clip case.

FIG. 9A is a cross-sectional view illustrating a primary part of the ligating apparatus at the protruding of a clip. FIG. 9B is a cross-sectional view illustrating the primary part at the position-adjustment of a body tissue. FIG. 9C is a cross-sectional view illustrating the primary part at the supporting of the body tissue with the clip by clipping the body tissue.

FIG. 10A is a cross-sectional view illustrating a primary part of the ligating apparatus at the pulling-in of the clip. FIG. 10B is a cross-sectional view illustrating the primary part at the separating of the clip.

DETAILED DESCRIPTION OF EMBODIMENTS OF THE INVENTION

Hereinafter, embodiments of the invention are described with reference to the drawings.

Figure 1:
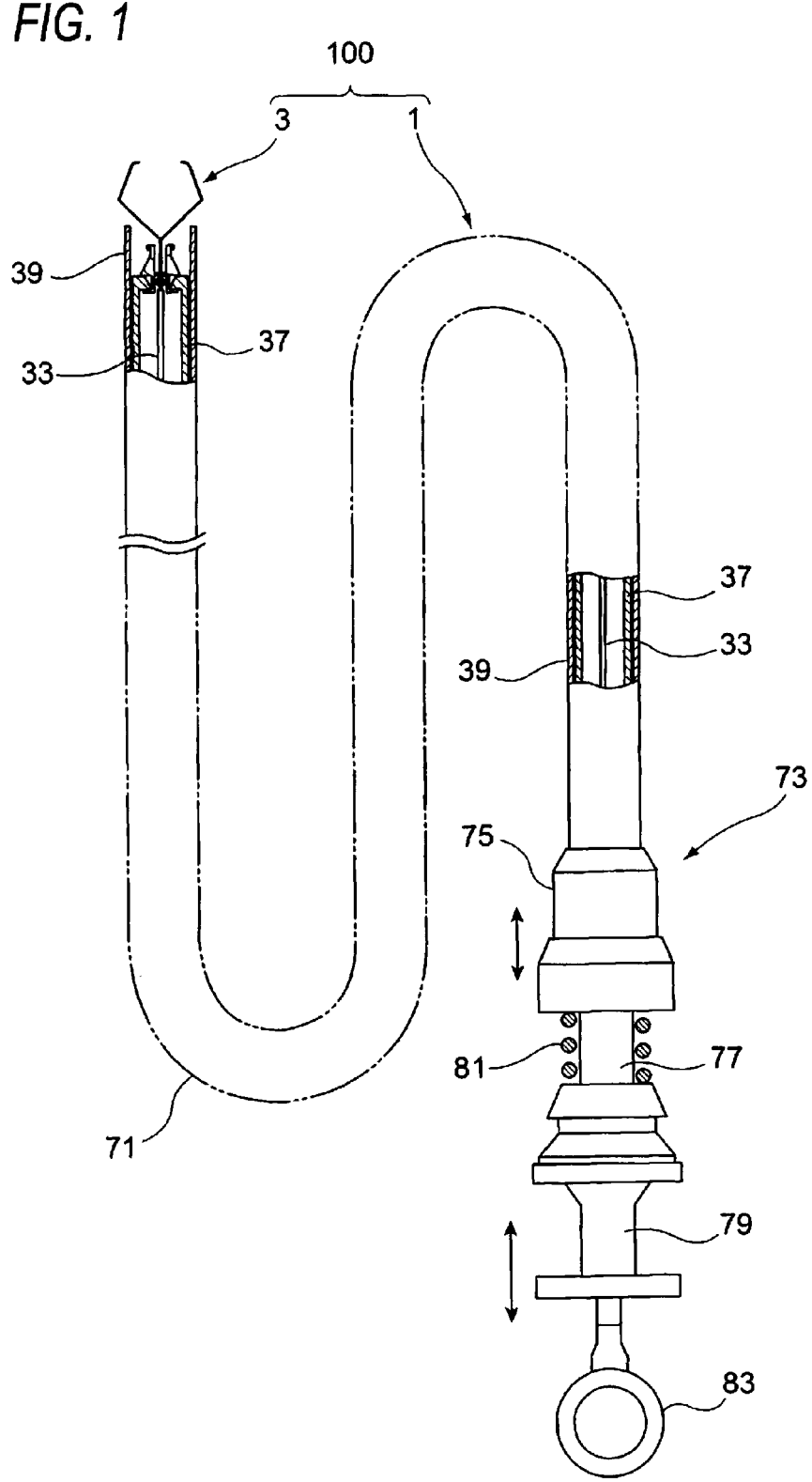
FIG. 1 is a partly cutaway plan view of a ligating apparatus, which is a diagram for illustrating an embodiment of the invention.

FIG. 1 is a partly cutaway plan view of a ligating apparatus, which is a diagram for illustrating an embodiment of the invention.

A ligating apparatus 100 is configured by including an operating device 1, and a clip unit 3. The ligating apparatus is configured to be supplied with a new clip from a clip case which will be described below. The operating device 1 is configured to include an inserting portion 71 and a proximal side operating portion 73. The inserting portion 71 is configured to include an outer sheath member 39, an inner sheath member 37 inserted into the outer sheath member 39, and an operating wire 33 inserted into the inner sheath member 37. The proximal side operating portion 73 is configured to include an outer sheath connecting element 75 fixed to the proximal side of the outer sheath member 39, an operating portion body 77 for performing advancing/retreating operations of the inner sheath member 37 with respect to the outer sheath member 39, a slider portion 79 for performing advancing/retreating operations of the operating wire 33 with respect to the inner sheath member 37, a slider spring 81 provided between the outer sheath connecting element 75 and the slider portion 79, and a finger hook ring 83.

The operating device 1 is such that the inner sheath member 37 is protruded from the outer sheath member 39 when the operating portion body 77 is pressed towards the distal end thereof while the outer sheath connecting element 75 is fixed, and that on the other hand, the outer sheath member 39 is protruded from the inner sheath member 37 when the operating portion body 77 is pulled thereinto. When the slider portion 79 is moved in a direction away from the finger hook ring 83, the operating wire 33 is pulled into the inner sheath member 37. On the other hand, when the slider portion 79 is moved closer to the finger hook ring 83, the operating wire 33 protrudes from the inner sheath member 37. The operating wire 33 is formed of a metal twisted wire made of stainless steel, NiTi-alloy or the like having appropriate elasticity. The above clip unit 3 is detachably attached to an inner sheath distal-end portion 35 in which the operating wire 33 can be advanced and retreated.

Figure 2:
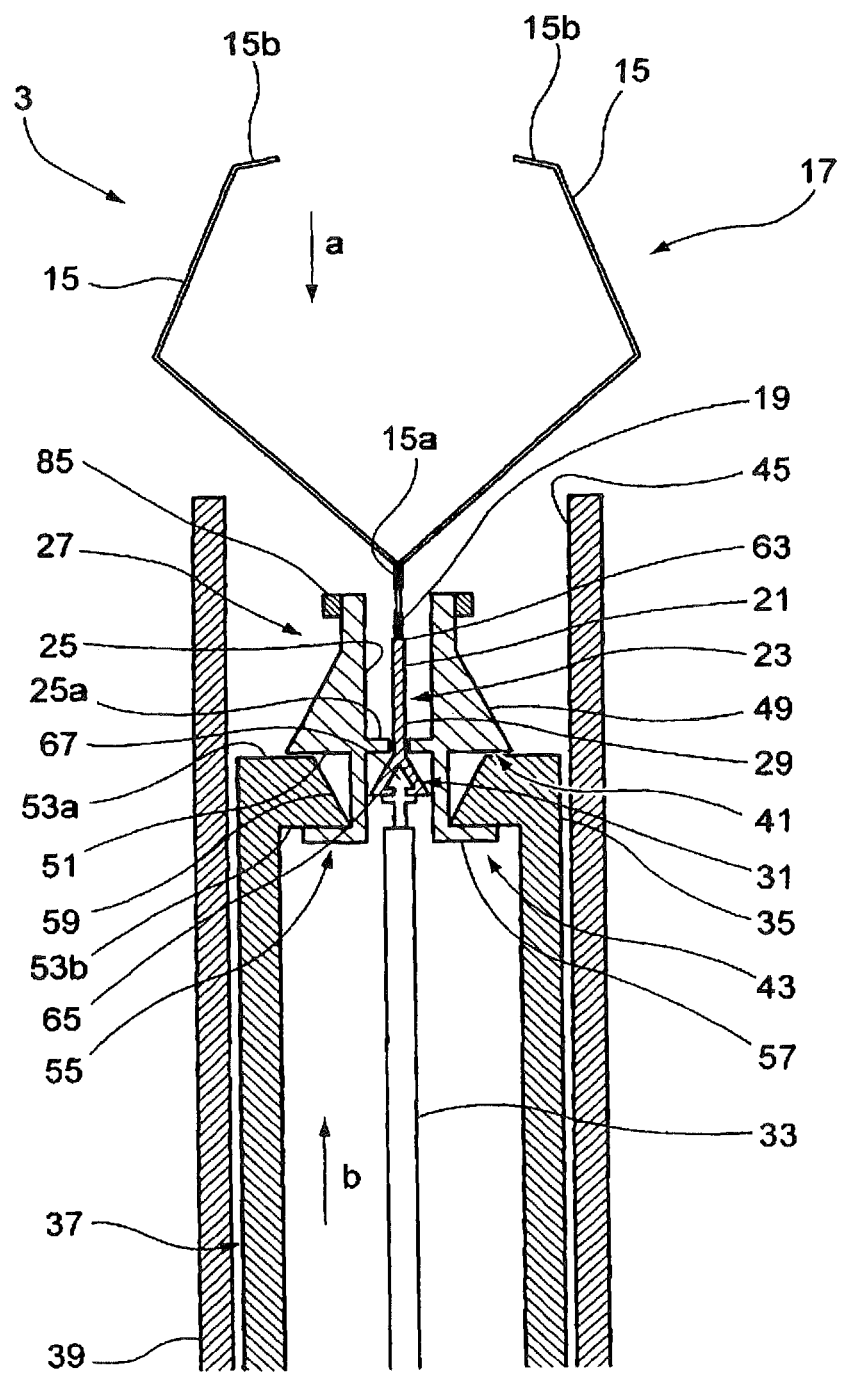
FIG. 2 is a cross-sectional view of a distal end portion of the ligating apparatus illustrated in FIG. 1.

FIG. 2 is a cross-sectional view of the distal end portion of the ligating apparatus illustrated in FIG. 1.

The clip unit 3 includes a clip 17, a clip connecting member 23, a clip holding member 27, a first movement restricting portion 41, and a second movement restricting portion 43. The clip 17 includes openable/closable arm portions 15 for ligating a body tissue. A body tissue is ligated by the arm portions 15. The arm portions 15 are formed like a pair of open leg elements by outwardly bending each metal plate member made of metal, such as stainless steel, having appropriate spring properties at a central portion thereof. An intersecting portion 15a is formed at a back end of each arm portion 15. A tissue grasping portion 15b is formed at the distal end portion of each arm portion 15. In the present specification, a side in a direction in which the ligating apparatus 100 is inserted is referred as a front side. The side opposite to the front side is referred to as a back side.

The clip connecting member 23 is continuously connected to a clip base portion 19 serving as a back end of the intersecting portion 15a. The clip connecting member 23 is such that a connecting member distal-end portion 21 serving as a distal end of the clip connecting member 23 is connected to the clip base portion 19. The clip connecting member 23 is made of a high-strength resin material, e.g., nylon (trademark) and formed cylindrically. A fragile portion which will be described below is provided between the connecting member distal-end portion 21 and the clip base portion 19. That is, the clip 17 and the clip connecting member 23 are configured to be connected to each other via the fragile portion. A wire connecting portion 31 is provided in the connecting member base portion 29 of the clip connecting member 23. The wire connecting portion 31 is formed as a conical diameter-increased portion 65 formed by connecting the top part of a hollow conical body continuously to the connecting member base portion 29.

The conical diameter-increased portion 65 serves to spread the elastically bending leg-element which will be described below. An engaging hole which will be described below is bored in a back end surface of the conical diameter-increased portion 65. The engaging hole is such that an arrowhead-like distal-end portion 67 provided at the distal end portion of the operating wire 33 can detachably be inserted thereinto. The arrowhead-like distal-end portion 67 is caught in the engaging hole of the conical diameter-increased portion 65 by barb parts provided at the back end parts of the conical diameter-increased portion 65, so that the arrowhead-like distal-end portion 67 is restricted from being disengaged therefrom. Accordingly, the clip 17 is connected to the operating wire 33 by the clip connecting member 23 and the arrowhead-like distal-end portion 65 caught in the conical diameter-increased portion 65.

A disengagement restricting force generated by the arrowhead-like distal-end portion 67 is set to be larger than the strength of the fragile portion. This is because the wire is prevented from being disengaged before the fragile portion is fractured. When the clip 17 is separated from the clip connecting member 23 by fracturing the fragile portion 63, the clip connecting member 23 is connected to the operating wire 33 and taken out of the body cavity while the arrowhead-like distal-end portion 67 remains caught therein. The clip connecting member 23 taken out therefrom is disengaged from the arrowhead-like distal-end portion 67 with a finger or the like by a predetermined extracting force.

The clip holding member 27 includes a conical body portion 49 provided at a front part thereof and an elastically bending leg-element 55 provided posterior to the conical body portion 97. The clip holding member 23 also includes a communicating hole 21 extending in a direction along an axis line of the conical body portion 49 to pass the clip 17 and the clip connecting member 23 therethrough. The clip holding member 27 is formed by, e.g., performing injection molding on a resin. A narrowing portion 25a is provided in the communicating hole 25. A more front portion of the clip connecting member 23 than the conical diameter-increased portion 65 is inserted through the narrowing portion 25a. That is, the conical diameter-increased portion 65 abuts against the narrowing portion 25a to thereby restrict the clip connecting member 23 from being slipped off more frontwardly therefrom. On the other hand, the narrowing portion 25a allows the backward extraction of the connecting member distal-end portion 21.

Figure 3:
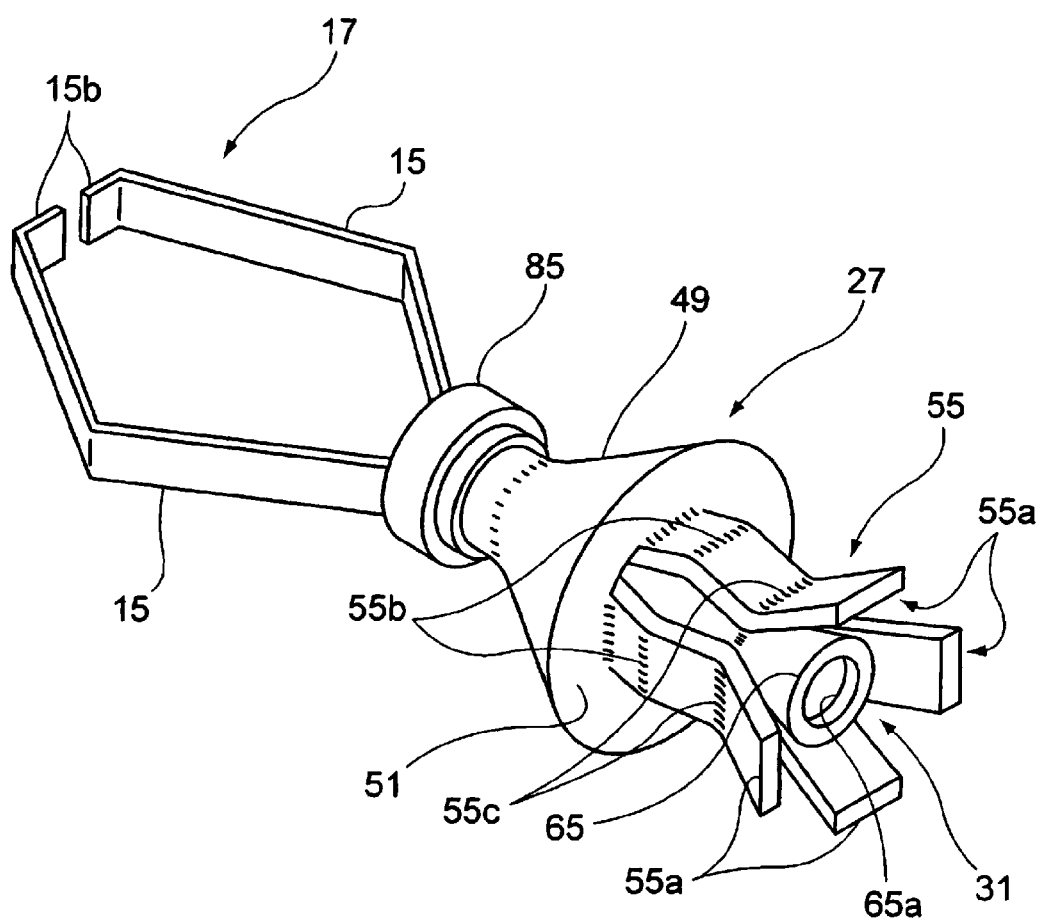
FIG. 3 is a perspective view of a clip unit illustrated in FIG. 2.

FIG. 3 is a perspective view of the clip unit 3 illustrated in FIG. 2.

An abutment ring 85 is formed at the front part of the conical body portion 49 coaxially with the communicating hole 25. The abutment ring 85 abuts against a separating wall portion serving as a stopper portion of a clip case which will be described below. An elastically bending leg-element 55 protruding backwardly from a back end surface of the conical body portion 49 are such that four leg portions 55*a* are radially arranged. Each leg portion 55*a* includes an inner bending point 55*b* and an outer bending point 55*c* arranged backwardly from the back end surface of the conical body portion 49 in this order. Each leg portion 55*a* is bent at the inner bending point 55*b* serving as a base point towards the inside of the communicating hole 25. The inside diameter of each leg portion 55*a* at the outer bending point 55*c* is less than the outside diameter of the conical diameter-increased portion 65. In addition, each leg portion 55*a* is folded at the outer bending point 55*c* serving as a base point to direct the associated leg portion 55*a* outwardly. The leg portions 55*a* of the elastically bending leg-element 55 are radially arranged, so that a substantially conical central space is formed to a back end side posterior to the outer bending point 55*c*. In the central space, the conical diameter-increased portion 65 is arranged. An engaging hole 65*a* through which the above arrowhead-like distal-end portion 67 is detachably inserted is opened in the back end surface of the conical diameter-increased portion 65.

That is, the conical diameter-increased portion 65 arranged in the central space is configured to spread out, when pressed by the operating wire 33, the outer bending point 55*c* of each leg portion 55*a* to thereby advance. The advancement of the conical diameter-increased portion 65 causes the back end part of each leg portion 55*a* to open in a direction substantially perpendicular to the central axis of the communicating hole 25 by employing the outer bending point 55*c* as a base point. The back end of each opened leg portion 55*a* is caught in a distal-end narrowing portion 59 of an inner sheath distal-end portion which will be described below.

Turning back to FIG. 2, each of the outer sheath member 39 and the inner sheath member 37 can be configured by, e.g., a coil sheath having flexibility, which is obtained by closely coiling a spring-property material. The outer sheath member 39 is arranged to cover the outer periphery of the inner sheath member 37. The inner sheath member 37 freely advances and retreats in the outer sheath member 39. That is, the outer sheath member 39 is arranged to freely advance and retreat with respect to the inner sheath member 37. The inside diameter of the outer sheath member 39 is set such that each arm portion 15 can abut against the distal-end portion 35 of the inner peripheral surface 45 thereof. Thus, the outer sheath member 39 works to change the degree of opening of the arm portions 15. The inner sheath member 37 is extended to enclose the operating wire 33, and has the distal-end narrowing portion 59 provided at the distal-end portion 35 to protrude to the inside of the inner sheath member 37. The distal-end narrowing portion 59 abuts against the back end surface of the conical body portion 49 on a distal-end-side bearing surface 53*a* thereof to support the conical body portion 49. The distal-end narrowing portion 59 abuts against the back end part of each opened leg portion 55*a* on a back-end-side bearing surface 53*b* thereof to support each leg portion 55*a*. Thus, the clip holding member 27 is axially supported by and fixed to the distal end part of the inner sheath member 37. The operating wire 33 inserted in the inner sheath member 37 performs an operation of pulling the clip connecting member 23 to thereby freely operate the clip 17 in an advancing/retreating direction.

The ligating apparatus 100 includes the first movement restricting portion 41 and the second movement restricting portion 43, which restrict the movement of the clip holding member 27 with respect to the inner sheath member 37. The first movement restricting portion 41 restricts the movement of the clip holding member 27 to the axially back end side (i.e., in a direction designated by arrow a) of the inner sheath member 37. The second movement restricting portion 43 restricts the movement of the clip holding member 27 to the axially distal end side (i.e., in a direction designated by arrow b) of the inner sheath member 37.

The first movement restricting portion 41 is formed on the bottom surface 51 of the conical body portion 49 which is formed in the clip holding member 27. The first movement restricting portion 41 is configured as a catching face that abuts against the distal-end bearing surface 53*a* of the distal-end narrowing portion 59. Consequently, the clip holding member 27 is restricted from moving in the direction of arrow a.

The second movement restricting portion 43 is formed as the elastically bending leg-element 55 extended towards the inner sheath member 37 from the communicating hole 25 of the clip holding member 27. The elastically bending leg-element 55 is spread out when the conical diameter-increased portion 65 of the clip connecting member 23 is inserted into the communicating hole 25. A leg back-end portion 57 abuts against the back-end-side bearing surface 53*b* of the distal-end narrowing portion 59 of the inner sheath member 37. Accordingly, the distal-end narrowing portion 59 of the inner sheath member 37 is sandwiched between the bottom surface 51, which is the back end surface of the conical body portion 49, and the leg back-end portion 57 of each leg portion 55*a*. That is, the inner sheath member 37 and the clip 17 can be fixed to each other by spreading out the elastically bending leg-element 55.

When the clip 17 is taken out of the communicating hole 25 of the clip holding member 27, i.e., when the conical diameter-increased portion 65 of the clip connecting member 23 is taken out of the communicating hole 25, the elastically bending leg-element 55 is elastically returned to a state before spreading out the leg-element 55. That is, the engagement between the inner sheath member 37 and the clip holding member 27 or the release of the engagement therebetween can be performed depending upon whether the conical diameter-increased portion 65 is inserted into a distal-end-side space defined by the leg portions 55*a*.

The clip 17 is inserted into the communicating hole 25 of the clip holding member 27 by pulling the operating wire 33. Thus, the degree of opening of the arm portions 15 is fixed. For example, when the clip 17 is inserted into the communicating hole 25 by pulling the operating wire 33, a back part of the clip 17 is narrowed at the front-part opening edge of the communicating hole 25. The arm portion 15 is fixed in a closed state.

The clip connecting member 23 includes the fragile portion 63 which can be fractured when the operating wire 33 is further pulled after the clip 17 is inserted into the communicating hole 25 of the clip holding member 27 by pulling the operating wire 33, as described above. The fragile portion 63 is formed as a fracturing portion to have a small diameter. The size of a cross-section of the fragile portion 63 is set so that the fragile portion 63 is fractured when a rupture force of about 20 newtons (N) to about 60N is applied thereto. When the fragile portion 63 is fractured, the clip 17 and the operating wire 33 are separated from each other. That is, the clip 17 can be separated from the operating wire 33 in a state, in which a body tissue 11 is clipped by the clip 17, by pulling the operating wire 33.

The clip connecting member 23 includes the above conical diameter-increased portion 65 for spreading out the elastically bending leg-element 55. The arrowhead-like distal-end portion 67 of the operating wire 33 is detachably inserted into the conical diameter-increased portion 65. The formation of the conical diameter-increased portion 65 in the clip connecting member 23 negates the diameter-increasing effect of the conical diameter-increased portion 65 on the elastically bending leg-element 55 after the clip connecting member 23 is taken out of the clip holding member 27. Consequently, the elastically bending leg-element 55 is elastically restored to automatically release the connection between the clip holding member 27 and the inner sheath member 37. Accordingly, the clip holding member 27 is indwelt in the body together with the clip 17 clipping a body tissue. The conical diameter-increased portion 65 is such that the arrowhead-like distal-end portion 67 of the operating wire 33 can easily be connected thereto by being detachably snap-inserted or that after separated from the clip 17, the conical diameter-increased portion 65 can be detached from and attached to the arrowhead-like distal-end portion 67.

Next, the clip case is described hereinafter.

Figure 4:
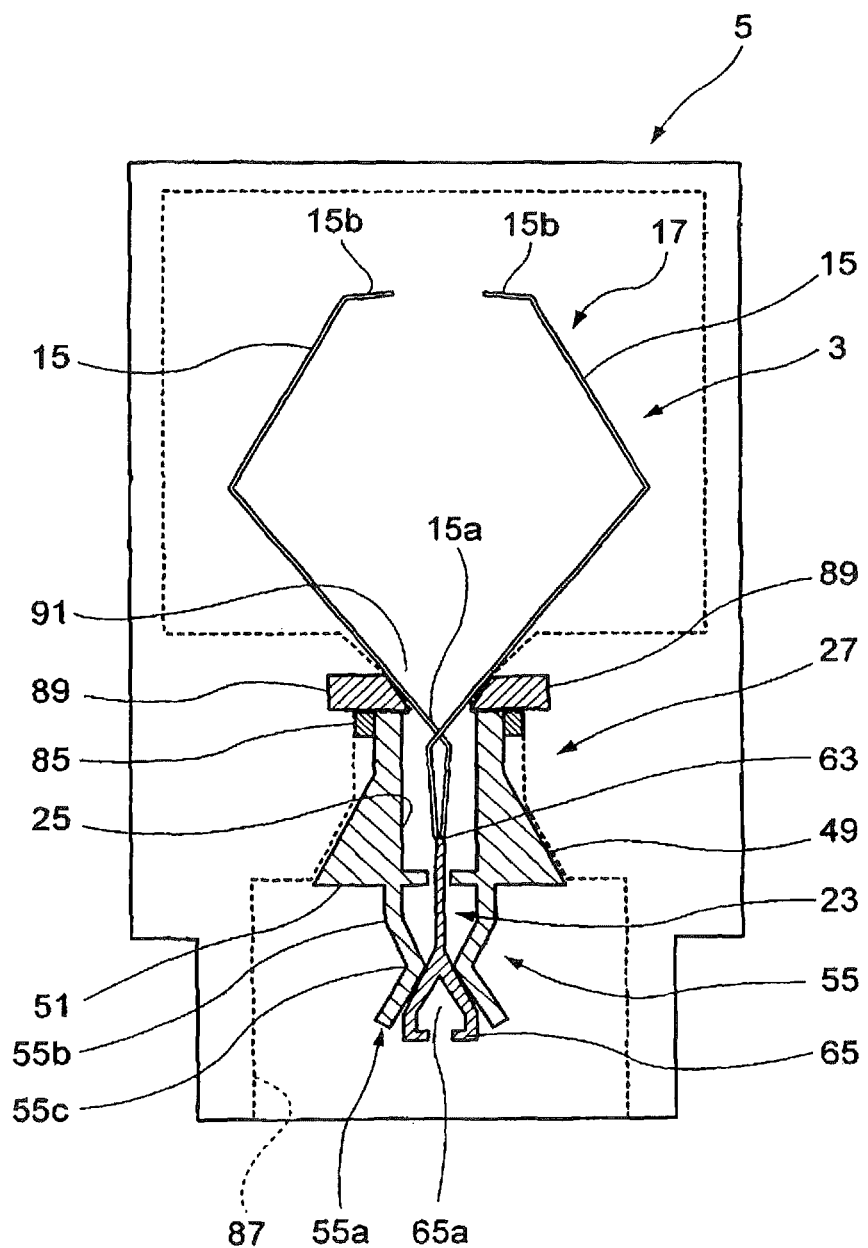
FIG. 4 is a plan view illustrating a clip case accommodating the clip unit.
Figure 5:
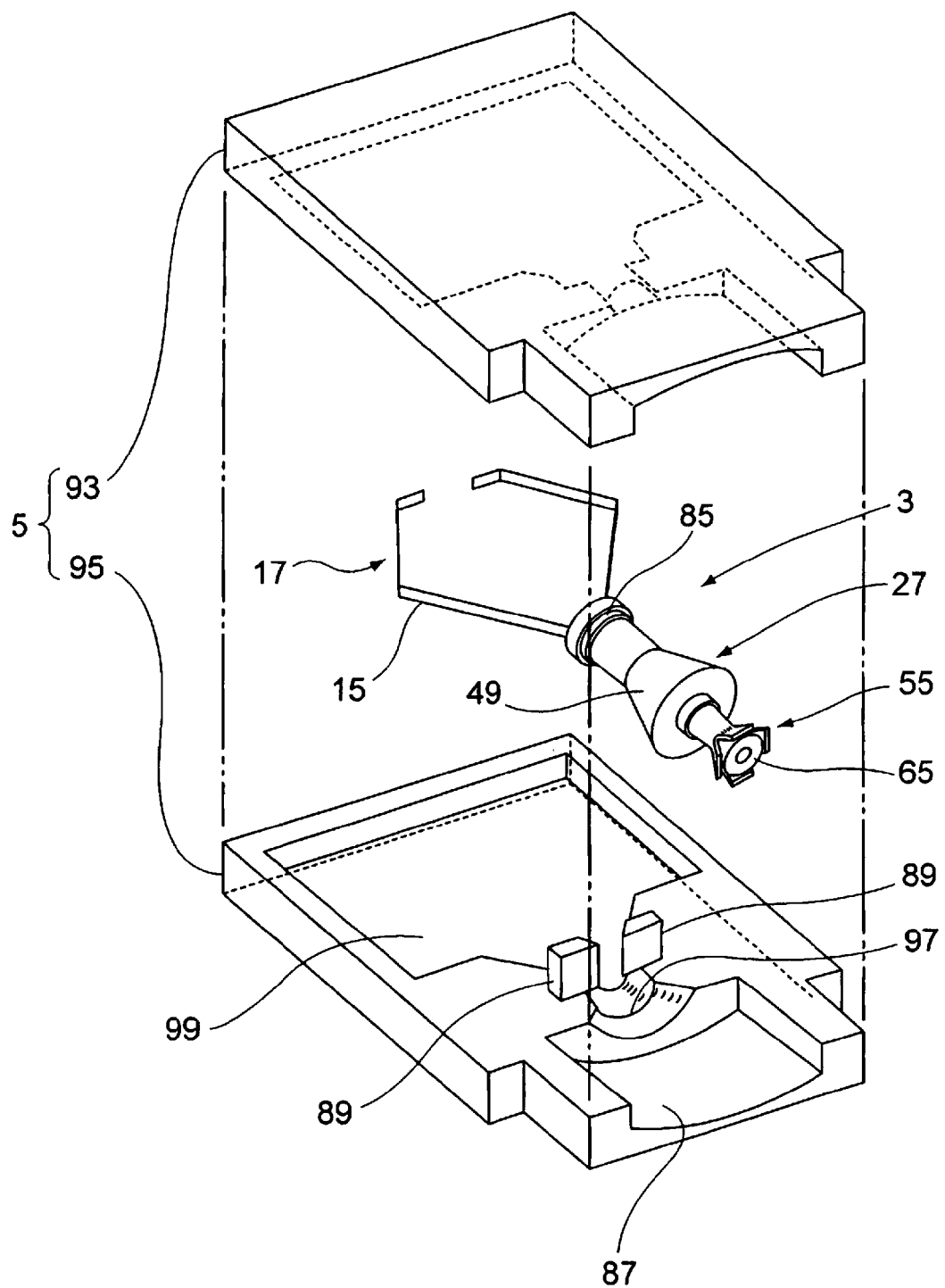
FIG. 5 is an exploded perspective view of the clip case illustrated in FIG. 4.

FIG. 4 is a plan view of the clip case that accommodates the clip unit. FIG. 5 is an exploded perspective view of the clip case illustrated in FIG. 4.

As illustrated in FIGS. 4 and 5, the clip unit 3 is housed in the clip case 5. The clip case 5 includes a pair of upper and lower cases and is formed into a flat substantially-rectangular shape. After the assembly of each of each of the upper and lower cases, a sheath insertion opening portion 87 into which the inner sheath member 37 is inserted is formed in one side surface in the longitudinal direction of the clip case 5. Spaced wall portions 89 serving as a pair of ribs are provided at a front part of the sheath insertion opening portion 87. The abutment ring 85 of the clip holding member 27 abuts on the spaced wall portions 89 from the sheath insertion opening portion 87. The clip unit 3 is such that the back part of the opened clip 17 is arranged in the gap 91 between the spaced wall portions 89 in a state in which the abutment ring 85 abuts on the spaced wall portions 89. The clip unit 3 is held in the clip case 5 by sandwiching the spaced wall portions 89 between the back part of the clip 17 and the abutment ring 85.

The clip case 5 includes the upper case 93 and the lower case 95 each of which has substantially the same shape and is manufactured by injection-molding of a transparent resin having appropriate hardness. As illustrated in FIG. 5, a holding concave portion 97 for holding the conical body portion 49 of the clip holding member 27 is formed between each spaced wall portion 89 and the sheath insertion opening portion 87. A front part of the holding concave portion 97 communicates with an arm accommodating portion 99 hosing the arm portion 15 of the clip 17.

Next, an operation of the ligating apparatus 100 having the above configuration is described hereinafter.

FIG. 6A is a cross-sectional view illustrating a primary part of the ligating apparatus 100 at the position-adjustment of the operating device 1 and the clip unit 3. FIG. 6B is a cross-sectional view illustrating the primary part at the projecting of the inner sheath member 37. FIG. 6C is a cross-sectional view illustrating the primary part at the abutment of the wire 33.

First, in order to attached to the ligating apparatus 100, as illustrated in FIG. 6A, the position of the inner sheath member 37 is adjusted to the sheath insertion opening portion 87 of the clip case 5 housing the clip unit 3. In the sheath insertion opening portion 87, the elastically bending leg-element 55 of the clip unit 3 preliminarily set in the clip case 5 is arranged.

When the operating portion body 77 is pressed into the outer sheath connecting element 75 illustrated in FIG. 1, the inner sheath member 37 protrudes and enters the sheath insertion opening portion 87, as illustrated in FIG. 6B. A leg portion introducing hole 101 is formed like a tapered hole in the distal inner sheath distal-end portion 35. Thus, the elastically bending leg-element 55 smoothly enters the inner sheath distal-end portion 35. Next, the finger hook ring 83 is pressed into the slider portion 79. Thus, as illustrated in FIG. 6C, the operating wire 33 protrudes, so that the arrowhead-like distal-end portion 67 provided at the distal end of the operating wire 33 hits against the conical diameter-increased portion 65 of the clip connecting member 23.

Incidentally, it is possible that the distal end of the inner sheath member 37 is preliminarily set to protrude from the distal end of the outer sheath member 39 and that the distal end of the inner sheath member 37 is inserted directly into the sheath insertion opening portion 87 of the clip case 5.

FIG. 7A is a cross-sectional view illustrating a primary part of the ligating apparatus 100 at the start of pressing the wire 33. FIG. 7B is a cross-sectional view illustrating the primary part at the spreading of the elastically bending leg-element 55. FIG. 7C is a cross-sectional view illustrating the primary part at the taking-out of the clip unit 3 from the clip case 5.

When the finger hook ring 83 illustrated in FIG. 1 is further forwardly moved in a state in which the arrowhead-like distal-end portion 67 provided at the distal end of the operating wire 33 abuts against the conical diameter-increased portion 65 of the clip connecting member 23 as illustrated in FIG. 7A, the arrowhead-like distal-end portion 67 enters and is caught in the conical diameter-increased portion 65; because the distal end of the clip holding member 27 is restricted by the spaced wall portions 89. In addition, the conical diameter-increased portion 65 enters a deep portion of each elastically bending leg-element 55, as illustrated in FIG. 7B. That is, the conical diameter-increased portion 65 passes through a bent part and enters the deep portion of each elastically bending leg-element 55. Thus, the leg back-end portions 57 are spread substantially perpendicularly to the wire 33 and caught by the back surface of the inner sheath distal-end portion 35. Because the distal end of the conical diameter-increased portion 65 abuts against the narrowing portion 25a of the communicating hole 25, the clip unit 3 stops at a position at which the leg portions 55a are spread. Consequently, the clip unit 3 is held in the operating device 1 by being restricted from being disengaged from the inner sheath member 37. The operating device 1 is retreated with respect to the clip case 5 in a state in which the clip unit 3 is held in the inner sheath member 37, as illustrated in FIG. 7C. Thus, the arm portion 15 of the clip 17 is elastically deformed and passes through the gap 91.

Figure 8A:
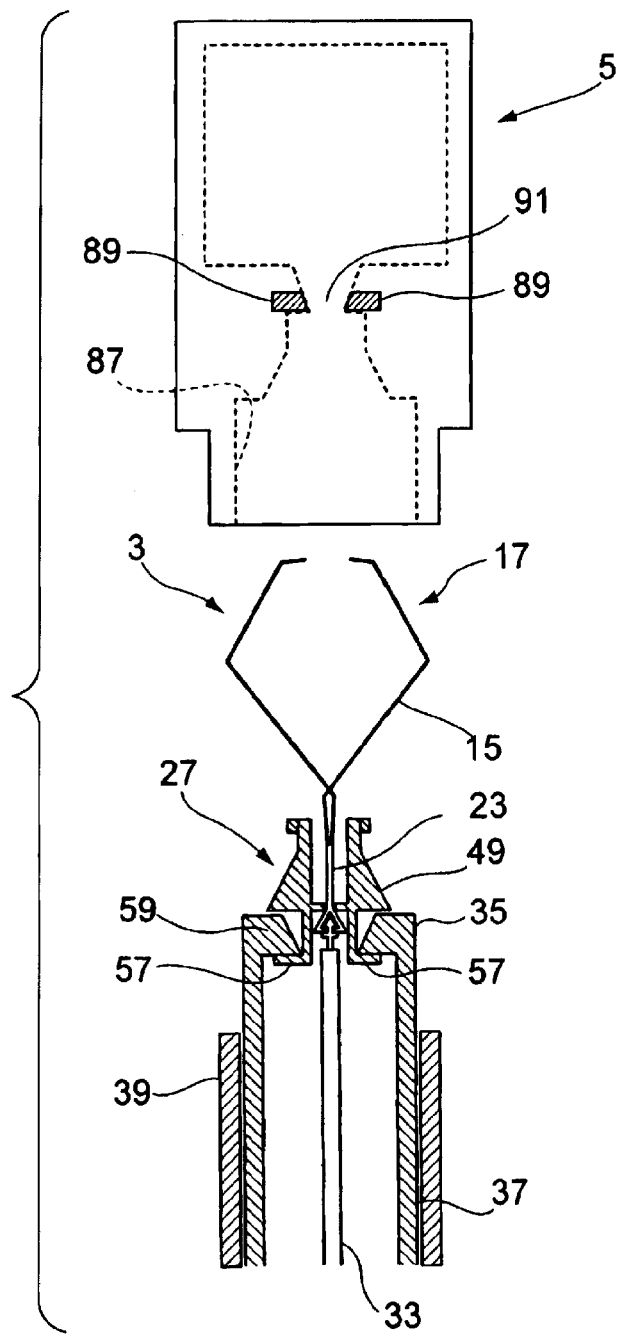
FIG. 8A is a cross-sectional view illustrating a primary part of the ligating apparatus after the taking-out of the clip unit from the clip case.
Figure 8B:
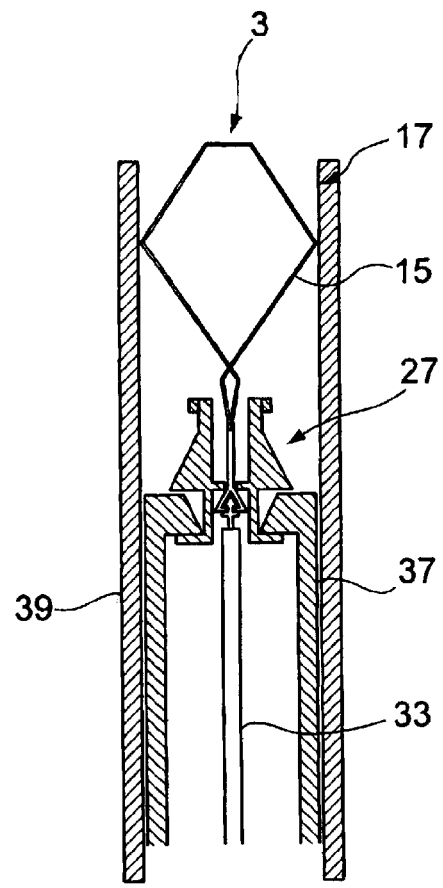
FIG. 8B is a cross-sectional view illustrating the primary part at the fitting of an outer sheath member on the clip.

FIG. 8A is a cross-sectional view illustrating a primary part of the ligating apparatus 100 after the taking-out of the clip unit 3 from the clip case 5. FIG. 8B is a cross-sectional view illustrating the primary part at the fitting of the outer sheath member 39 on the clip 17.

When the clip 17 passing through the gap 91 is completely taken out of the clip case 5, the leg-element 55 thereof is spread again by an elastically restoring force, as illustrated in FIG. 8A. When the outer sheath connecting element 75 is spaced from the slider portion 79 by the elastically restoring force of the slider spring 81, the operating portion body 77 is retreated with respect to the outer sheath connecting element 75. Consequently, as illustrated in FIG. 8B, the inner sheath member 37 pulls the clip unit 3 into the outer sheath member 39. Accordingly, the clip 17 put in a state in which the leg is closed is housed in the outer sheath member 39. Thus, preparation for inserting, into the body cavity, the operating device 1 provided with the clip unit 3 is completed.

Next, an operation of regrasping the clip 17 and that of ligating the tissue with the clip 17 are described hereinafter.

FIG. 9A is a cross-sectional view illustrating a primary part of the ligating apparatus 100 at the projecting of the clip 17. FIG. 9B is a cross-sectional view illustrating the primary part at the position-adjustment of the body tissue 11. FIG. 9C is a cross-sectional view illustrating the primary part at the supporting of the body tissue 11 with the clip 17 by clipping the body tissue 11.

In order to ligate the body tissue 11 with the clip unit 3, the distal end part of the inserting portion 71 of the operating device 1 is introduced into the body cavity via a channel of an endoscope (not shown) preliminarily inserted into the body cavity. Then, the distal end of the inserting portion 71 is introduced to a target part while the inside of the body cavity is observed with the endoscope. When it is confirmed that the distal end of the inserting portion 71 is introduced to the target part, the operating portion body 77 is pressed thereinto. When the operating portion body 77 is pressed thereinto, the inner sheath member 37 advances in the outer sheath member 39. Consequently, as illustrated in FIG. 9A, the clip 17 protrudes from the outer sheath member 39. The leg of the protruded clip 17 is spread by an elastically restoring force to form a clipping gap 103 between the tissue grasping portions 15*b*, 15*b*.

Then, the positioning of the clip 17 is performed such that the body tissue 11 is arranged in the clipping gap 103, as illustrated in FIG. 9B. When a force for pressing the operating portion body 77 is loosened in a state in which the position of the tissue grasping portion 15*b* is optimal, the outer sheath member 39 advances to the inner sheath member 37 by the elastically restoring force of the slider spring 81. Consequently, as illustrated in FIG. 9C, the arm portions 15 of the clip 17 are pulled into the outer sheath member 39. Thus, the body tissue 11 is clipped with the tissue grasping portion 15*b*.

If a grasping position at which the tissue grasping portion 15*b* grasps the body tissue 11 is changed at that time, the inner sheath member 37 is protruded again by pressing the operating portion body 77. Thus, the diameter reducing effect of the outer sheath member 39 on the arm portions 15 is canceled. That is, the ligating apparatus 100 is returned to the state illustrated in FIG. 9B, in which the tissue grasping portion 15*b* is opened so that the grasping position can iteratively be changed.

This is implemented due to that the clip unit 3 is held in the inner sheath distal-end portion 35. The clip unit 3 is such that the bottom surface 51 of the conical body portion 49 abuts against the inner sheath bearing surface 53*a*. Thus, the movement in the direction of arrow a of the clip holding member 27 is restricted. The leg back-end portion 57 is caught by the back surface of the inner sheath distal-end portion 35. Thus, the movement in the direction of arrow b of the clip holding member 27 is restricted. That is, the clip unit 3 is surely held by sandwiching the inner sheath distal-end portion 35. Thus, the clip unit 3 does not slip off.

FIG. 10A is a cross-sectional view illustrating a primary part of the ligating apparatus 100 at the pulling-in of the clip 17. FIG. 10B is a cross-sectional view illustrating the primary part at the separating of the clip 17.

When the grasping position at which the tissue 11 is grasped by the tissue grasping portion 15*b* is definitely determined, the slider portion 79 is pulled. Then, as illustrated in FIG. 10A, the clip connecting member 23 is pulled via the operating wire 33. The clip unit 3 pulled with the operating wire 33 is such that the bottom surface 51 of the conical body portion 49 abuts against the bearing surface 53*a* of the inner sheath member 37 to thereby restrict the retreat of the clip holding member 27. On the other hand, the clip 17 connected continuously to the clip connecting member 23 is pulled into the communicating hole 25 while the tissue grasping portion 15*b* grasps the body tissue 11. Thus, a larger grasping force acts upon the tissue grasping portion 15*b*.

The clip connecting member 23 pulled with the operating wire 33 pulls the fragile portion 63 and the clip base portion 19 into the narrowing portion 25*a*. Simultaneously with this, the conical diameter-increased portion 65 slips off the elastically bending leg-element 55. Thus, the elastically bending leg-element 55 is narrowed. The narrowing of the elastically bending leg-element 55 cancels the catching of the clip unit 3 by the leg back-end portion 57. However, a pulling force due to the operating wire 33 acts upon the entire clip unit 3. Thus, the clip unit 3 does not slip off the inner sheath distal-end portion 35. When the clip base portion 19 passes through the narrowing portion 25*a* as illustrated in FIG. 10B, a reaction force exerted on the arm portions 15 from the opening edge of the communicating hole 25 increases. Accordingly, a pulling resistance force increases. If the pulling resistance force exceeds a predetermined value, the fragile portion 63 is fractured. Thus, the clip base portion 19 and the clip connecting member 23 are separated from each other.

The clip unit 3 separated from the clip connecting member 23 is such that the arm portions 15 are sufficiently pulled into the clip holding member 27. Thus, the clip 17 does not slip off frontwardly from the clip holding member 27. Accordingly, the clip 17 retains a state in which the clip 17 clips the body tissue 11. The clip unit 3 whose arm portions 15 are restricted by the clip holding member 27 from being opened is indwelt in the body, together with the clip holding member 27, as it is.

Thus, the ligating apparatus 100 is such that the clip holding member 27 is restricted from being axially moved with respect to the inner sheath member 37. Consequently, the ligating apparatus 100 can prevent the slip-off of the clip 17 and the relative movement between the operating wire 33 and the inner sheath member 37 from occurring when the arm portions 15 of the clip 17 are opened and closed by the outer sheath member 39. Accordingly, the handleability of the ligating apparatus 100 can be enhanced.

Accordingly, according to the above ligating apparatus 100 in which a plurality of clips 17 can be sequentially replaced, when an operation of ligating the body tissue 11 is performed, operations of opening and closing of the clip 17 can freely be performed. In addition, the regrasping of the body tissue 11 can be performed by a simple operation.

Next, a modification of the ligating apparatus 100 of the above configuration is described below.

Figure 11:
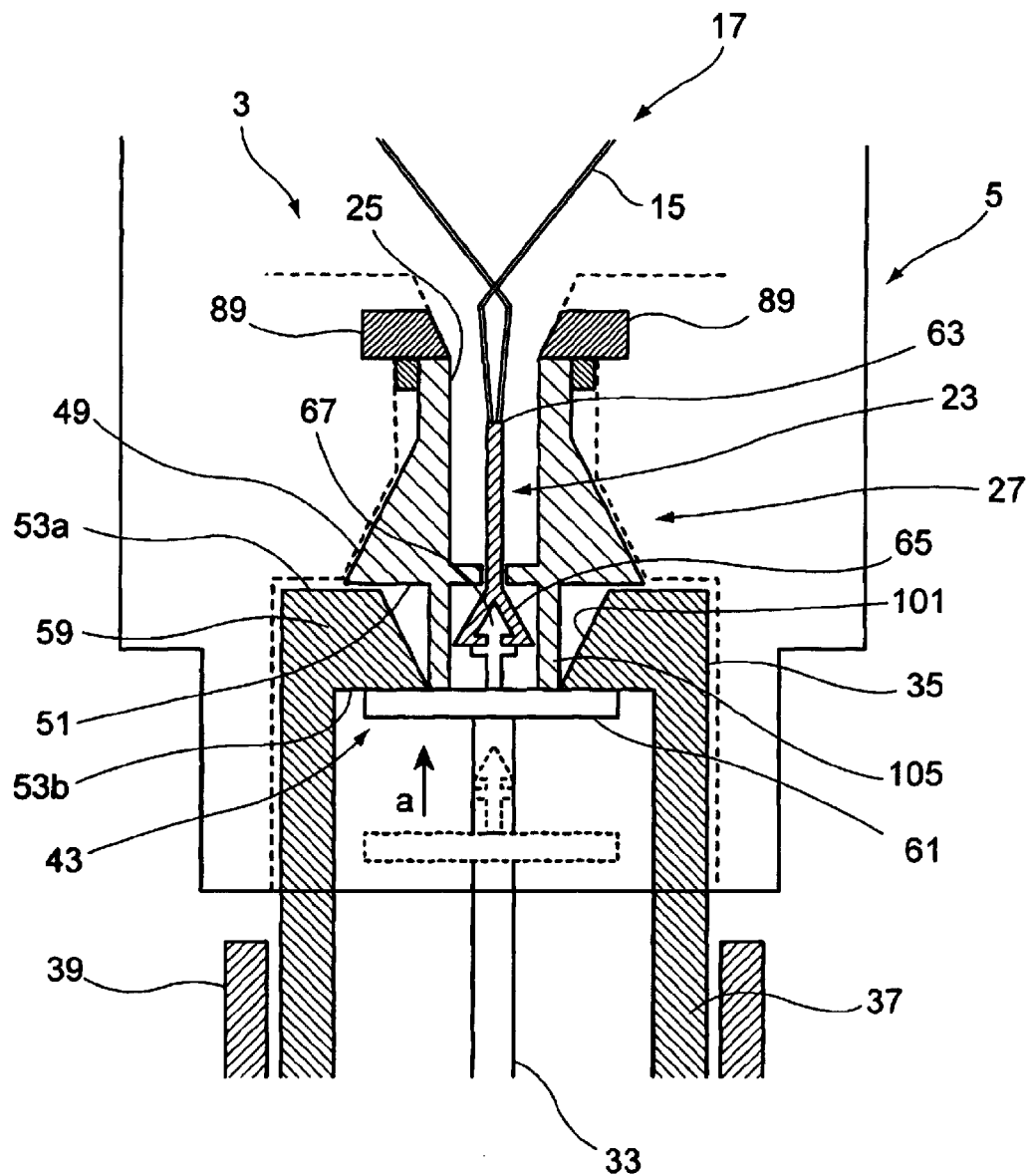
FIG. 11 is a cross-sectional view illustrating a ligating apparatus according to a modification using an abutment flange as a second movement restricting portion.

FIG. 11 is a cross-sectional view illustrating a primary part of the ligating apparatus 100 according to a modification using an abutment flange as a second movement restricting portion. A member which is the same member as an associated one of members illustrated in FIGS. 1 to 10 is designated with the same reference numeral as that used to designate the associated one of the members. A redundant description of such an element is omitted.

This modification is such that the second movement restricting portion 43 is formed as an abutment flange 61 fixed to the operating wire 33. The abutment flange 61 and the bottom surface 51 of the conical body portion 49 sandwich a distal-end narrowing portion 59 of the inner sheath member 37. A cylindrical portion 105 is protruded from the bottom surface 51 of the conical body portion 49 coaxially with the communicating hole 25. The cylindrical portion 105 is arranged in the leg portion introducing hole 101.

According to this modification, the clip holding member 27 is restricted by the abutment flange 61 from being moved in the direction of arrow a radially frontwardly from the inner sheath member 37. Accordingly, according to this modification, the structure of the clip holding member 27 can be simplified by omitting the elastically bending leg-element 55.

Thus, the invention is not limited to the above embodiments. The invention is intended to be susceptible to modifications and applications made by those skilled in the art based on the descriptions of the specification and known technology. The modifications and the applications are included within a scope of protection.

As described above, the following items are disclosed in the present specification.

(1) A ligating apparatus for ligating a body tissue includes a clip, a clip connecting member, a clip holding member, an operating wire, an inner sheath member, an outer sheath member and first and second movement restricting portions. The clip has freely openable/closable arm portions and configures to ligate a body tissue with the arm portions. The clip connecting member has a connecting member end portion connected continuously to a clip base portion. The clip holding member has a communicating hole for causing the clip and the clip connecting member to be inserted into the communicating hole. The operating wire connects to a wire connecting portion provided at a connecting member base portion of the clip connecting member and is configured to perform an operation of pulling the clip connecting member. The inner sheath member is configured to be extended to enclose the operating wire and supports the clip holding member at a distal-end portion of the inner sheath member. The outer sheath member is arranged to cover outer periphery of the inner sheath member and is arranged to freely advance and retreat. The first and second movement restricting portions are configured to restrict movements of the clip holding member with respect to the inner sheath member. The outer sheath member changes a degree of opening of the arm portions by causing the arm portions to abut on an inner peripheral surface of the outer sheath member. The first movement restricting portion restricts movement of the clip holding member from an axially outer side to an axially inner side. The second movement restricting portion restricts movement of the clip holding member from an axially inner side to an axially outer side.

According to this ligating apparatus, the clip holding member is restricted from being axially moved with respect to the inner sheath member. Thus, the slip-off of the clip and the relative movement between the operating wire and the inner sheath member can be prevented from occurring when the arm portions of the clip are opened and closed by the outer sheath member. Consequently, the handleability of the ligating apparatus can be enhanced.

(2) The ligating apparatus according to (1), the first movement restricting portion includes catching-surfaces respectively formed on the clip holding member and the inner sheath member to abut against each other.

According to this ligating apparatus, the movement of the clip holding member is surely restricted by causing the clip holding member to abut against each catching surface.

(3) The ligating apparatus according to (2), the catching-surfaces include a bottom surface of a conical body portion formed in the clip holding member and an inner sheath bearing surface formed on the distal-end portion of the inner sheath member.

According to this ligating apparatus, the movement of the clip holding member is surely restricted by causing the conical body portion of the clip holding member to hit against the inner sheath bearing surface of the inner sheath member.

(4) The ligating apparatus according (3), the second movement restricting portion includes an elastically bending leg-element extended from the communicating hole of the clip holding member to the inner sheath member. The elastically bending leg-element is spread when the clip connecting member is inserted into the communicating hole. An end narrowing portion of the inner sheath member is sandwiched by a leg end portion of the leg-element and the bottom surface of the conical body portion.

According to this ligating apparatus, the elastically bending leg-element is spread. Thus, the inner sheath member and the clip can be fixed.

(5) The ligating apparatus according to (4), when the clip is taken out of the communicating hole of the clip holding member, the elastically bending leg-element is elastically returned to a state before the leg-element is spread.

According to this ligating apparatus, the clip holding member can be engaged with or disengaged from the inner sheath member, depending upon whether the insertion of the elastically bending leg-element into the communication hole is performed or not.

(6) The ligating apparatus according to any one of (1) to (3), the second movement restricting portion includes an abutment flange fixed to the operating wire. The abutment flange and the bottom surface of the conical body portion sandwich the end narrowing portion of the inner sheath member.

According to this ligating apparatus, the movement of the clip holding member from an inner side to an outer side in the direction of an axis of the inner sheath member is restricted.

(7) The ligating apparatus according to any one of (1) to (6), the clip is inserted into the communicating hole of the clip holding member by pulling the operating wire so that the degree of opening of the arm portions is fixed.

According to this ligating apparatus, the clip is inserted into the communicating hole by pulling the operating wire. Thus, the arm portions can be put into a closed state.

(8) The ligating apparatus according to (7), the clip connecting member includes a fragile portion whose fracture occurs when the operating wire is further pulled after the clip is inserted into the communicating hole of the clip holding member by pulling the operating wire. The clip and the operating wire are separated from each other when the fracture of the fragile portion occurs.

According to this ligating apparatus, the operating wire is pulled after a body tissue is ligated by the clip. Accordingly, the clip is separated from the operating wire while being in a state in which the clip clips the body tissue.

(9) The ligating apparatus according to any one of (1) to (8), the clip connecting member includes a conical diameter-increased portion for spreading the elastic bending leg-element. An arrowhead-like end portion of the operating wire is detachably inserted into an inside of the conical diameter-increased portion.

According to this ligating apparatus, the conical diameter-increased portion is formed in the clip connecting member. Thus, after the clip connecting member is taken out of the clip holding member, the diameter increasing effect of the conical diameter-increased portion wears off. The elastically bending leg-element elastically restores. The connection between the clip holding member and the inner sheath member is automatically released. In addition, the operating wire can easily be connected to the clip connecting member by being detachably snap-inserted. Alternatively, after separated from the clip, the clip connecting member can be detached from and attached to the operating wire.

(10) A ligating apparatus for ligating a body tissue includes an outer sheath member, an inner sheath member, a front-end narrowing portion, an operating wire, a clip, a clip connecting member, a clip holding member, a first movement restricting portion and a second movement restricting portion. The outer sheath member includes a front-end, a back-end, and a longitudinal axis. The inner sheath member is provided in the outer sheath member to freely advance and retreat. The front-end narrowing portion is provided at a front-end of the inner sheath member to protrude radially inwardly and includes a front-end-side bearing surface portion placed at a front-end-side of the front-end narrowing portion and a back-end-side bearing surface placed at a back-end-side of the front-end narrowing portion. The operating wire is provided in the inner sheath member to freely advance and retreat. The clip has freely openable/closable arm portions and a base part which connects bases of the arm portions and configures to ligate a body tissue with the arm portions. The clip connecting member has a clip connecting portion connected to a base portion of the clip and an operating wire connecting portion connected to a front-end of the operating wire. The clip holding member has a communicating hole for causing the clip and the clip connecting member to be inserted into the communicating hole. The first movement restricting portion is provided on the clip holding member and is configured to have an outside diameter which is smaller than an inside diameter of the outer sheath member and larger than an outside diameter of a front-end opening portion of the inner sheath member. The second movement restricting portion is provided on one of the clip holding member and the operating wire and is configured to have an outside diameter which is smaller than an inside diameter of the inner sheath member and larger than an inside diameter of the front-end narrowing portion of the inner sheath member. When the clip connecting member and the operating wire are connected to each other, the front-end narrowing portion of the inner sheath member is arranged between the first movement restricting portion and the second movement restricting portion. The clip holding member is axially fixed to a front-end of the inner sheath member.

According to this ligating apparatus, the clip holding member can be axially fixed to the distal end of the inner sheath member. Thus, a body tissue can smoothly be ligated with the clip by advancing the outer sheath member to the inner sheath member, while the clip is prevented from slipping off.

(11) The ligating apparatus according to (10), the second movement restricting portion includes at least two leg portions which are radially provided at a back-end part of the clip holding portion. The clip connecting portion includes a diameter-increased part in the operating wire connecting portion. The diameter-increased part of the clip connecting member is pressed into between the leg portions to thereby cause the leg portions to be radially spread and to abut against a back-end-side bearing surface part of the front-end narrowing portion of the inner sheath member.

According to this ligating apparatus, the diameter-increased portion of the clip connecting member is pressed into among the leg portions of the clip holding member and then spread. The narrowing portion provided at the distal end of the inner sheath member is sandwiched among the clip holding member and the leg portions.

(12) The ligating apparatus according to (10), the second movement restricting portion includes a diameter-increased portion provided in the operating wire. The diameter-increased portion is caused by connecting the clip connecting member and the operating wire to abut against a back-end-side bearing surface part of the front-end narrowing portion of the inner sheath member.

According to this ligating apparatus, the narrowing portion provided at the distal end of the inner sheath member is sandwiched between the diameter-increased portion provided in the wire and the clip holding member.

What is claimed is:

1. A ligating apparatus for ligating a body tissue, said apparatus comprising:
    a clip that comprises freely openable/closeable arm portions and that is configured to ligate a body tissue with the arm portions;
    a clip connecting member that comprises a connecting member end portion connected continuously to a clip base portion;
    a clip holding member that comprises a communicating hole for causing the clip and the clip connecting member to be inserted into the communicating hole;
    an operating wire that connects to a wire connecting portion provided at a connecting member base portion of the clip connecting member and that is configured to perform an operation of pulling the clip connecting member;
    an inner sheath member that is configured to be extended to enclose the operating wire and that supports the clip holding member at a distal-end portion of the inner sheath member;
    an outer sheath member that is arranged to cover an outer periphery of the inner sheath member and that is arranged to freely advance and retreat; and
    first and second movement restricting portion that are configured to restrict movements of the clip holding member with respect to the inner sheath member,
    wherein the outer sheath member changes a degree of opening of the arm portions by causing the arm portions to abut on an inner peripheral surface of the outer sheath member,
    wherein the first movement restricting portion restricts a movement of the clip holding member in a direction toward an axially back end side of the inner sheath member,
    wherein the second movement restricting portion restricts a movement of the clip holding member in a direction toward an axially distal end side of the inner sheath member,
    wherein the first movement restricting portion includes catching-surfaces respectively formed on the clip holding member and the inner sheath member to abut against each other,
    wherein the catching-surfaces include a bottom surface of a conical body portion formed in the clip holding member and an inner sheath bearing surface formed on the distal-end portion of the inner sheath member,
    wherein the second movement restricting portion includes an elastically bending leg-element extended from the communicating hole of the clip holding member to the inner sheath member,
    wherein the elastically bending leg-element is spread when the clip connecting member is inserted into the communicating hole, and
    wherein an end narrowing portion of the inner sheath member is sandwiched by a leg end portion of the leg-element and the bottom surface of the conical body portion.

2. The ligating apparatus according to claim 1, wherein, when the clip is taken out of the communicating hole of the clip holding member, the elastically bending leg-element is elastically returned to a state before the leg-element is spread.

3. The ligating apparatus according to claim 1, wherein the second movement restricting portion includes an abutment flange fixed to the operating wire, and
    wherein the abutment flange and the bottom surface of the conical body portion sandwich the end narrowing portion of the inner sheath member.

4. The ligating apparatus according to claim 1, wherein the clip is inserted into the communicating hole of the clip holding member by pulling the operating wire so that the degree of opening of the arm portions is fixed.

5. The ligating apparatus according to claim 4, wherein the clip connecting member includes a fragile portion whose fracture occurs when the operating wire is further pulled after the clip is inserted into the communicating hole of the clip holding member by pulling the operating wire, and
wherein the clip and the operating wire are separated from each other when the fracture of the fragile portion occurs.

6. The ligating apparatus according to claim 1, wherein the clip connecting member includes a conical diameter-increased portion for spreading the elastically bending leg-element, and
wherein an arrowhead-like end portion of the operating wire is detachably inserted into an inside of the conical diameter-increased portion.

7. A ligating apparatus for ligating a body tissue, said ligating apparatus comprising:
an outer sheath member that includes a front-end, a back-end, and a longitudinal axis;
an inner sheath member that is provided in the outer sheath member to freely advance and retreat;
a front-end narrowing portion that is provided at a front-end of the inner sheath member to protrude radially inwardly and that includes a front-end-side bearing surface portion placed at a front-end-side of the front-end narrowing portion and a back-end-side bearing surface placed at a back-end-side of the front-end narrowing portion;
an operating wire that is provided in the inner sheath member to freely advance and retreat;
a clip that comprises freely openable/closable arm portions and a base part which connects bases of the arm portions and that configures to ligate a body tissue with the arm portions;
a clip connecting member that comprises a clip connecting portion connected to a base portion of the clip and an operating wire connecting portion connected to a front-end of the operating wire;
a clip holding member that comprises a communicating hole for causing the clip and the clip connecting member to be inserted into the communicating hole;
a first movement restricting portion that is provided on the clip holding member and that is configured to have an outside diameter which is smaller than an inside diameter of the outer sheath member and larger than an outside diameter of a front-end opening portion of the inner sheath member; and
a second movement restricting portion that is provided on one of the clip holding member and the operating wire and that is configured to have an outside diameter which is smaller than an inside diameter of the inner sheath member and larger than an inside diameter of the front-end narrowing portion of the inner sheath member,
wherein, when the clip connecting member and the operating wire are connected to each other, the front-end narrowing portion of the inner sheath member is arranged between the first movement restricting portion and the second movement restricting portion, and
wherein the clip holding member is axially fixed to a front-end of the inner sheath member.

8. The ligating apparatus according to claim 7, wherein the second movement restricting portion includes at least two leg portions which are radially provided at a back-end part of the clip holding portion,
wherein the clip connecting portion includes a diameter-increased part in the operating wire connecting portion, and
wherein the diameter-increased part of the clip connecting member is pressed into between the leg portions to thereby cause the leg portions to be radially spread and to abut against a back-end-side bearing surface part of the front-end narrowing portion of the inner sheath member.

9. The ligating apparatus according to claim 7, wherein the second movement restricting portion includes a diameter-increased portion provided in the operating wire, and
wherein the diameter-increased portion is caused by connecting the clip connecting member and the operating wire to abut against a back-end-side bearing surface part of the front-end narrowing portion of the inner sheath member.

* * * * *